United States Patent
Lauryssen

(10) Patent No.: US 9,301,849 B2
(45) Date of Patent: Apr. 5, 2016

(54) ENDPLATE PUNCH TEMPLATE AND METHOD OF USE

(71) Applicant: Warsaw Orthopedic, Inc., Warsaw, IN (US)

(72) Inventor: Carl Lauryssen, Beverly Hills, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 395 days.

(21) Appl. No.: 13/829,002

(22) Filed: Mar. 14, 2013

(65) Prior Publication Data

US 2014/0277458 A1 Sep. 18, 2014

(51) Int. Cl.
- *A61F 2/44* (2006.01)
- *A61B 17/16* (2006.01)
- *A61F 2/30* (2006.01)
- *A61B 17/88* (2006.01)

(52) U.S. Cl.
CPC .............. *A61F 2/44* (2013.01); *A61B 17/1604* (2013.01); *A61B 17/1671* (2013.01); *A61F 2/442* (2013.01); *A61F 2/4455* (2013.01); *A61B 17/885* (2013.01); *A61F 2/4405* (2013.01); *A61F 2002/3008* (2013.01); *A61F 2002/30062* (2013.01); *A61F 2002/30092* (2013.01); *A61F 2002/3093* (2013.01); *A61F 2002/30677* (2013.01); *A61F 2002/30892* (2013.01)

(58) Field of Classification Search
CPC ................. A61B 17/1671; A61B 17/1604
USPC .................. 606/184–186, 206, 207
See application file for complete search history.

(56) References Cited

U.S. PATENT DOCUMENTS

| | | | | |
|---|---|---|---|---|
| 4,997,432 A | * | 3/1991 | Keller | 623/17.11 |
| 5,250,067 A | * | 10/1993 | Gelfer et al. | 606/189 |
| 5,486,180 A | * | 1/1996 | Dietz et al. | 606/87 |
| 5,601,556 A | * | 2/1997 | Pisharodi | 606/86 A |
| 5,961,535 A | * | 10/1999 | Rosenberg et al. | 606/184 |
| 6,241,733 B1 | * | 6/2001 | Nicholson et al. | 606/84 |
| 6,692,501 B2 | | 2/2004 | Michelson | |
| 6,761,723 B2 | | 7/2004 | Buttermann et al. | |
| 6,840,941 B2 | | 1/2005 | Rogers et al. | |
| 7,611,514 B2 | | 11/2009 | Michelson | |
| 7,632,282 B2 | * | 12/2009 | Dinville | 606/99 |
| 7,645,281 B2 | | 1/2010 | Marik | |
| 7,766,918 B2 | | 8/2010 | Allard et al. | |
| 7,846,164 B2 | | 12/2010 | Castillo et al. | |
| 7,914,534 B2 | * | 3/2011 | Suddaby | 606/79 |
| 8,002,776 B2 | * | 8/2011 | Liu et al. | 606/85 |
| 8,221,425 B2 | * | 7/2012 | Arcenio et al. | 606/84 |
| 8,337,500 B2 | * | 12/2012 | Bertagnoli et al. | 606/80 |
| 2003/0032962 A1 | * | 2/2003 | McGahan et al. | 606/80 |
| 2003/0181915 A1 | | 9/2003 | Serhan | |
| 2003/0199874 A1 | * | 10/2003 | Michelson | 606/61 |

(Continued)

*Primary Examiner* — David Bates
(74) *Attorney, Agent, or Firm* — Sorell Lenna & Schmidt LLP

(57) ABSTRACT

An instrument for penetrating an endplate of a vertebra having a first plate including a first endplate engaging surface and a second surface. The first endplate engaging surface and the second surface are oriented so as to face in opposing directions. The first plate has a plurality of extensions projecting from the first endplate engaging surface to form a first extension template. The first extension template includes a centrally disposed extension and at least one extension radially disposed about the centrally disposed extension. The first extension template is configured to penetrate an endplate surface of a first vertebra when advanced into the endplate surface of the first vertebra.

17 Claims, 5 Drawing Sheets

(56) References Cited

U.S. PATENT DOCUMENTS

| | | | |
|---|---|---|---|
| 2003/0220645 A1* | 11/2003 | Suddaby | 606/79 |
| 2003/0225416 A1* | 12/2003 | Bonvallet et al. | 606/105 |
| 2004/0002711 A1 | 1/2004 | Berry | |
| 2004/0092941 A1* | 5/2004 | Jansen et al. | 606/84 |
| 2004/0162562 A1 | 8/2004 | Martz | |
| 2004/0215197 A1* | 10/2004 | Smith et al. | 606/79 |
| 2004/0215198 A1* | 10/2004 | Marnay et al. | 606/86 |
| 2004/0220582 A1* | 11/2004 | Keller | 606/99 |
| 2006/0247648 A1* | 11/2006 | Serbousek | 606/90 |
| 2007/0123907 A1* | 5/2007 | Weber | 606/99 |
| 2007/0270862 A1 | 11/2007 | Yu et al. | |
| 2007/0270863 A1* | 11/2007 | Melkent | 606/79 |
| 2007/0270956 A1* | 11/2007 | Heinz | 623/17.11 |
| 2009/0216329 A1 | 8/2009 | Lee et al. | |
| 2010/0145458 A1 | 6/2010 | Aferzon et al. | |
| 2010/0268343 A1 | 10/2010 | Dewey et al. | |
| 2010/0274299 A1* | 10/2010 | Lawson et al. | 606/86 R |
| 2011/0196373 A1* | 8/2011 | Jacob et al. | 606/79 |
| 2015/0105696 A1* | 4/2015 | Litke et al. | 600/587 |

\* cited by examiner

ENDPLATE PUNCH TEMPLATE AND METHOD OF USE

TECHNICAL FIELD

The present disclosure generally relates to medical devices, systems and methods for the treatment of musculoskeletal disorders, and more particularly to an endplate punch template that can be used to penetrate both endplates of a vertebra or the endplates of adjacent vertebrae during a surgical procedure.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. These treatments may require the penetration of both endplates of a given vertebra or the endplates of adjacent vertebra. This disclosure describes an improvement over prior art endplate penetration technologies.

SUMMARY OF THE INVENTION

Accordingly, an endplate punch template and methods of use are provided. It is contemplated that the endplate punch template may penetrate or perforate endplate surfaces in preparation for the fixation with interbody implant(s), and may also be used as a distracter. The endplate template can have either one plate or two opposing plates attached to a handle that, when actuated, advances the template(s) toward the endplates. Upon contact with the endplates the template penetrates into the endplates to create cavities that are complementary to the template. An interbody implant system including at least one spinal implant and the template discussed herein is also provided. The design on the template(s) is complementary to the design of extensions on at least one surface of the interbody implant so that cavities made in the endplates using the template mate with extensions on the surface of the implant. This mating relationship further locks the interbody implant in place and prevents slippage of the implant.

In one embodiment in accordance with the principles of the present disclosure, an instrument for penetrating an endplate of a vertebra is provided having a first plate including a first endplate engaging surface and a second surface. The first endplate engaging surface and the second surface are oriented so as to face in opposing directions. The first plate has a plurality of extensions projecting from the first endplate engaging surface to form a first extension template. The first extension template includes a centrally disposed extension and at least one extension radially disposed about the centrally disposed extension. The first extension template is configured to penetrate an endplate surface of a first vertebra when advanced into the endplate surface of the first vertebra.

In another embodiment in accordance with the principles of the present disclosure, an instrument for penetrating a vertebral endplate surface is provided. The instrument includes a first plate having a endplate engaging surface that includes a plurality of extensions projecting therefrom to form a first extension template. The first extension template has a centrally disposed extension and at least one extension radially disposed about the centrally disposed extension. The first extension template is configured to penetrate an endplate surface of a first vertebra when advanced into the endplate surface of the first vertebra. The instrument also includes a second plate having a endplate engaging surface comprising a plurality of extensions projecting therefrom to form a second extension template. The second extension template includes a centrally disposed extension and at least one extension radially disposed about the centrally disposed extension. The second extension template is configured to penetrate a second endplate surface when advanced into the second endplate surface. Each of the plurality of extensions have a leading end and a trailing end separated apart from one another by a continuous wall. The leading end of each extension projects from the first and second extension templates and is configured to penetrate the endplate surface of a vertebra.

In yet another embodiment of the present disclosure an interbody implant system is provided. The interbody implant system includes an instrument for penetrating an endplate surface of a vertebra. The instrument has a first plate including an endplate-engaging surface having a plurality of extensions projecting therefrom. The first extension template includes a centrally disposed extension and at least one extension radially disposed about the centrally disposed extension. The first extension template is configured to penetrate an endplate surface of a first vertebra so as to produce a complementary design to the template when advanced into the endplate surface of the vertebra. The instrument of the system also includes a second plate having an endplate engaging surface includes a plurality of extensions projecting from the endplate engaging surface to form a second extension template. The second extension template includes a centrally disposed extension and at least one extension radially disposed about the centrally disposed extension. Like the first extension template, the second extension template is configured to penetrate an endplate surface of a vertebra so as to produce a design complementary to the template when advanced into the endplate surface of the vertebra. Also included in the system is at least one interbody implant having at least one extension on at least one surface of the interbody implant that is configured to mate with at least part of the complementary design formed in the endplate surface of a vertebrae.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION OF THE INVENTION

Figure 1:
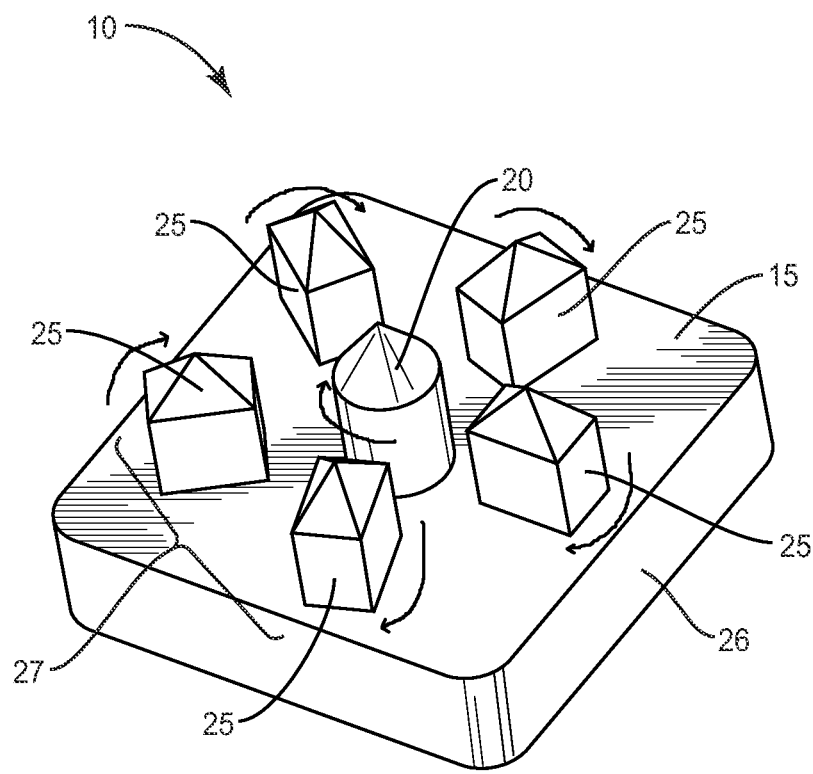
FIG. 1 is a perspective view of one particular embodiment of an endplate punch template in accordance with the principles of the present disclosure.
Figure 2:
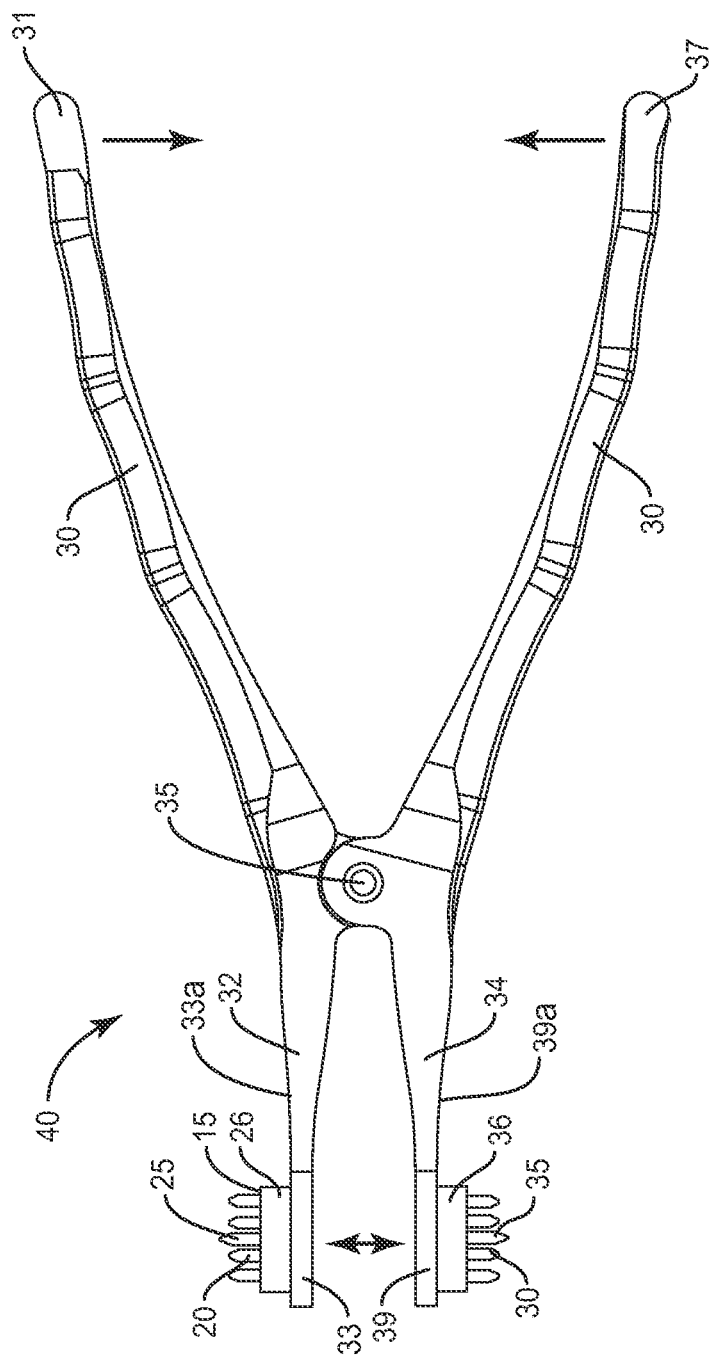
FIG. 2 is a perspective view of an instrument having first and second endplate punch templates shown in FIG. 1 and an endplate punch in accordance with the principles of the present disclosure.

The exemplary embodiments of the endplate punch template, and corresponding interbody implant system and related methods of use disclosed are discussed in terms of medical devices for the treatment of musculoskeletal disorders and more particularly in terms of implants that provide stabilization and height restoration for treating a vertebral column. It is envisioned that the endplate punch template and corresponding interbody implant system may be employed for fusion and fixation treatments to provide decompression, restoration of lordosis and resistance of subsidence into tissue, for example, vertebral endplates. It is further envisioned that the template and interbody implant system and methods of use disclosed can be employed to obtain fusion of vertebrae through a minimally invasive or percutaneous technique. In one embodiment, the disclosed endplate template punch and corresponding interbody implant system and methods of use can provide improved spinal treatment. It is contemplated that the interbody implant system and methods of use disclosed either provide an endplate punch template for penetrating into both endplates of a vertebra or the endplates of adjacent vertebrae and inserting an implant having extensions that correspond, at least in part, to the design of the template so as to lock the implant in place once inserted.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed endplate punch template and corresponding interbody implant system and methods of the present disclosure may be alternatively employed in a surgical treatment with a patient in a prone or supine position, and/or employ various surgical approaches to the spine, including anterior, posterior, posterior mid-line, medial, lateral, postero-lateral, and/or antero-lateral approaches, and in other body regions. The present disclosure may also be alternatively employed with procedures for treating the lumbar, cervical, thoracic and pelvic regions of a spinal column. The endplate punch template and interbody implant system and methods of the present disclosure may also be used on animals, bone models and other non-living substrates, such as, for example, in training, testing and demonstration.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "superior" and "inferior" are relative and used only in the context to the other, and are not necessarily "upper" and "lower".

Further, as used in the specification and including the appended claims, "treating" or "treatment" of a disease or condition refers to performing a procedure that may include administering one or more drugs to a patient in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a vertebral endplate punch template and implants having extensions that correspond, at least in part, to the specific design of the template and are configured to mate with the cavities created in the endplate by the template. Mating the implant with the cavities in the endplate reduces the chance that the implant can slip out of alignment thereby securing the implant in place in accordance with the principles of the present disclosure. Alternate embodiments are also disclosed. Reference will now be made in detail to the exemplary embodiments of the present disclosure, which are illustrated in the accompanying figures. Turning now to FIGS. 1-5B, there is illustrated components of a vertebral endplate punch and corresponding interbody implant system in accordance with the principles of the present disclosure.

The components of the interbody implant system can be fabricated from biologically acceptable materials suitable for medical applications, including metals, synthetic polymers, ceramics and bone material and/or their composites, depending on the particular application and/or preference of a medical practitioner. For example, the components of the endplate punch template, the instrument, including the endplate punch templates, as well as corresponding implants, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the interbody implant system may have material composites, including the above materials, to achieve various desired characteristics such as strength, rigidity, elasticity, compliance, biomechanical performance, durability and radiolucency or imaging preference. The components of the interbody implant system, individually or collectively, may also be fabricated from a heterogeneous material such as a combination of two or more of the above-described materials.

In one embodiment, shown in FIG. 1, a punch 10 is configured for penetrating an endplate surface of a vertebra and includes a plate 26 having an endplate engaging surface 15 including a plurality of extensions projecting therefrom to form a first extension template 27. First extension template 27 includes a centrally disposed extension 20 and at least one extension 25 radially disposed about centrally disposed extension 20. Extensions 20, 25 are configured to penetrate the endplate surface of a vertebra when advanced into the endplate surface. In one embodiment, the leading edges of extensions 20, can be pointed or have a sharp cutting edge so that extensions 20, 25 can cut into the surface of the endplate when advanced to create a plurality of cavities that correspond to the pattern of first extension template 27 of punch 10. The number and arrangement of the extensions 20, 25 can vary, as can the overall configuration of first extension template 27. That is, the number of extensions 20, 25, the shapes and sizes of extensions 20, 25, and the depths in which extensions 20, 25 will penetrate the endplate when advanced can vary and are within the scope of this disclosure. For example, extensions 20, 25 can have a cross-section selected from the group consisting of round, oval, polygonal, irregular, consistent, variable, uniform and non-uniform. In one embodiment, extensions 20, 25 may taper from a first diameter to a second diameter, wherein the first diameter is greater than the second diameter and terminate in a point configured to penetrate an endplate surface of a vertebra.

Punch 10 may be manipulated using an instrument 40 to position punch 10 adjacent a vertebral endplate and advance punch 10 into the vertebral endplate. In one embodiment in accordance with the disclosure of the present invention, shown in FIG. 2, instrument 40 includes a handle 30 having a first arm 32 and second arm 34 connected at a pivot point 35 such that first and second arms 32, 34 are moveable relative to one another. First arm 32 extends between a proximal end 31 and a distal end 33, and second arm 34 extends between a proximal end 37 and a distal end 39. Instrument 40 is configured such that that moving first and second arms 32, 34 so that proximal ends 31, 37 converge moves distal ends 33, 39 in opposite directions. That is, converging proximal ends 31, 37 moves distal ends 33, 39 apart from one another.

Distal end 33 of instrument 40 includes an outer surface 33a, and distal end 39 includes an outer surface 39a. Outer surface 33a of distal end 33 is configured to engage a first endplate surface, such as, for example, the lower vertebral endplate surface of an upper vertebral body, and outer surface 39a of distal end 39 is configured to engage a second endplate surface, such as, for example, an upper vertebral endplate surface of a lower vertebral body adjacent to the upper vertebral body. Punches, such as punch 10, for example, may be attached to outer surfaces 33a, 39a. In one embodiment, a first punch 10 is attached to outer surface 33a such that extensions 20, 25 face away from first arm 32 and a second punch 10 is attached to outer surface 33a such that extensions 20, 25 face away from second arm 34 such that causing proximal ends 31, 37 of instrument 40 to converge advances punches 10 away from each other and towards opposing endplate surfaces. Once extensions 20, 25 on punches 10 are in contact with the endplate surfaces, additional force advances extensions 20, 25 into the endplates so as to penetrate the endplate surface in order to create a plurality of cavities that correspond to the pattern of first extension template 27 of each punch 10. It is envisioned that instrument 40 may include punches having different extension templates such that after the surfaces of adjacent endplates are penetrated by the punches attached to outer surfaces 33a, 39a of instrument 40, one endplate will have cavities that correspond to the pattern of one extension template and the other endplate will have cavities that correspond to the pattern of the other, different extension template.

It is envisioned that instrument 40 may be configured to penetrate one endplate surface of a vertebra without penetrating an adjacent endplate surface of an adjacent vertebra. Accordingly, in one embodiment, instrument 40 may include punch 10 attached to outer surface 33a and a planar plate attached to outer surface 39a, or vice versa. Converging proximal ends 31, 37 of instrument 40 moves punch 10 on outer surface of 33a away from the planar plate such that punch 10 is advanced toward an endplate surface and the planar plate is advance toward an opposing endplate surface. Extensions 20, 25 on punch 10 penetrate the endplate surface in order to create a plurality of cavities that correspond to the pattern of first extension template 27 of punch 10. The planar plate is free of extensions such that the planar plate does not penetrate the endplate surface of the adjacent vertebra.

Figure 3:
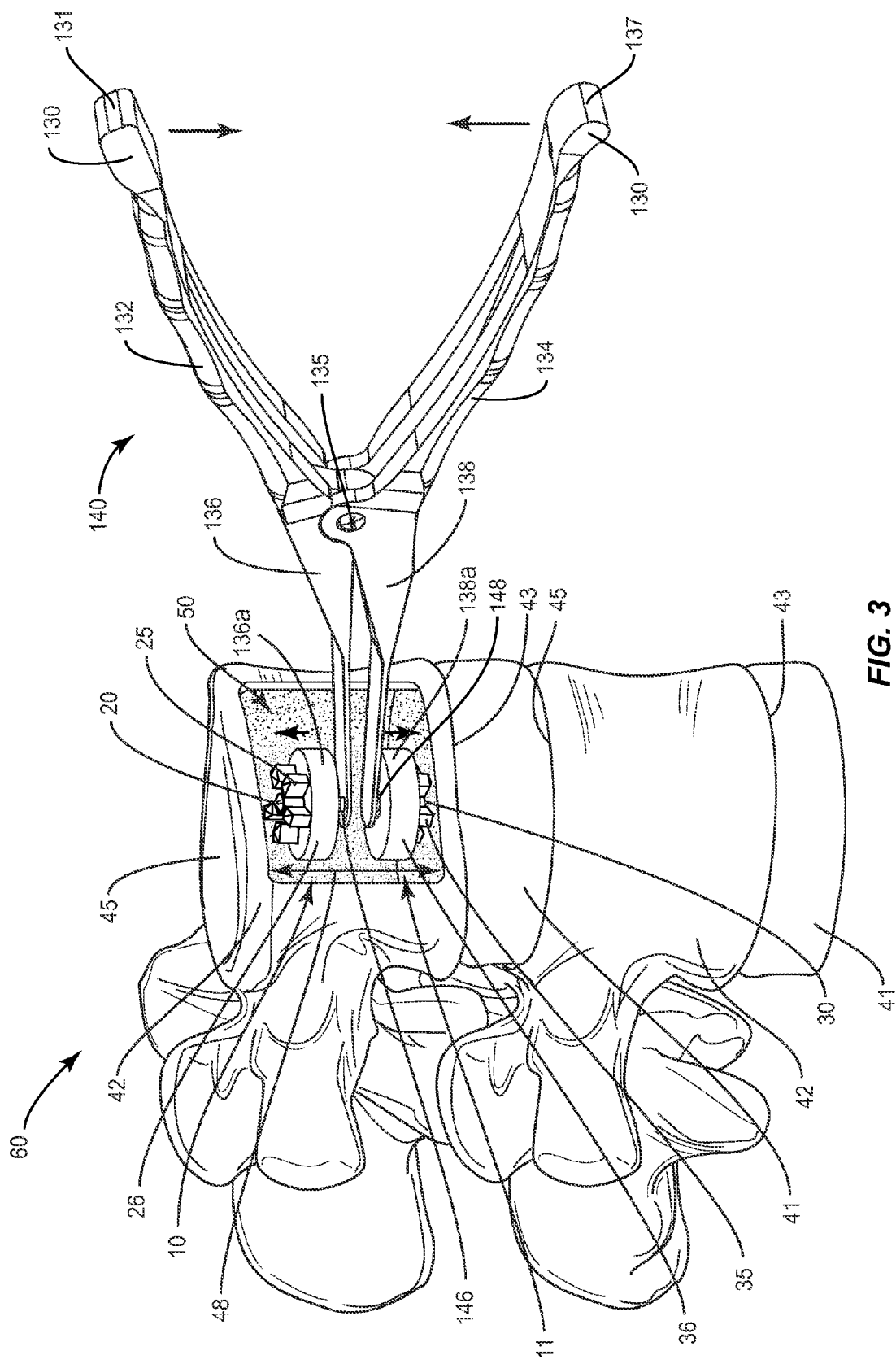
FIG. 3 is a side view of vertebrae with the instrument of FIG. 2 within the vertebral body.

In one embodiment in accordance with the disclosure of the present invention, shown in FIG. 3, an instrument 140 is configured to manipulate at least one punch, such as punch 10, to position the punch adjacent a vertebral endplate and advance the punch into the vertebral endplate. Instrument 140 has a configuration similar to that of instrument 40 and includes a handle 130 having a first arm 132 and second arm 134 connected at a first pivot point 135 such that first and second arms 132, 134 are moveable relative to one another. First arm 132 is connected to a first arm extension 136 such that first arm 132 and first arm extension 136 are moveable relative to one another. Second arm 134 is connected to a second arm extension 138 such that second arm 134 and second arm extension 138 are moveable relative to one another. First arm 132 includes a proximal end 131 and second arm 134 includes a proximal end 137. Instrument 140 is configured such that that moving first and second arms 132, 134 such that proximal ends 131, 137 converge moves first and second arm extensions 136, 138 in opposite directions. That is, converging proximal ends 131, 137 moves first and second arm extensions 136, 138 apart from one another.

First arm extension 136 of instrument 140 includes an outer surface 136a, and second arm extension 138 includes an outer surface 138a. Outer surface 136a of first arm extension 136 is configured to engage a first endplate surface, such as, for example, the lower vertebral endplate surface of an upper vertebral body, and outer surface 138a of second arm extension 138 is configured to engage a second endplate surface, such as, for example, an upper vertebral endplate surface of a lower vertebral body adjacent to the upper vertebral body. Punches, such as punch 10, for example, may be attached to outer surfaces 136a, 138a. The punches may be attached to outer surfaces 136a, 138a via axles 146, 148 such that the punches are rotatable about axles 146, 148 to allow a surgeon to orient an extension template on one of the punches relative to a vertebral endplate surface. In one embodiment, one punch 10 is attached to outer surface 136a such that extensions 20, 25 face away from first arm extension 136, and a punch 11 is attached to outer surface 138a. Punch 11 has a configuration similar to that of punch 10 and may be used for penetrating an endplate surface of a vertebra. Punch 11 includes a plate 36 having an endplate-engaging surface (not shown) including a plurality of extensions projecting therefrom to form a second extension template (not shown). Plate 36 has a height that is greater than that of plate 26. The second extension template includes an endplate engaging surface 38 including a centrally disposed extension 30 and at least one extension 35 radially disposed about centrally disposed extension 30. Extensions 30, 35 are configured to penetrate the endplate surface of a vertebra when advanced into the endplate surface. Punch 11 is attached to outer surface 138a of first arm extension 138 such that extensions 30, 35 face away from second arm extension 138. That is, converging proximal ends 131, 137 of instrument 140 advances punches 10, 11 away from each other and towards opposing endplate surfaces. Once extensions 20, 25 on punch 10 are in contact with a lower vertebral endplate surface and extensions 30, 35 are in contact with an endplate surface, such as the upper endplate surface of an adjacent vertebra, additional force advances extensions 20, 25 into the lower endplate surface in order to create a plurality of cavities therein that correspond to the pattern of first extension template 27. The additional force simultaneously advances extensions 30, 35 into the upper endplate surface so as to penetrate the same in order to create a plurality of cavities therein that correspond to the pattern of the second extension template.

As shown in FIG. 3, instrument 140 is inserted into a cavity 50 in a vertebra 42 of a spine 60 having a plurality vertebrae 42 separated by discs 41. Each vertebra 42 extends between an upper vertebral endplate 43 and a lower vertebral endplate 45. Instrument 140 is inserted into cavity 50 cut into one vertebra 42 such that extensions 20, 25 of punch 10 are positioned adjacent a lower surface of upper vertebral endplate 43 of vertebra 42 and extensions 30, 35 are positioned adjacent an upper surface of lower vertebral endplate 45 of the same vertebra. Proximal ends 131, 137 of instrument 140 are converged to advance punches 10, 11 away from each other at a defined distance 48, such that extensions 20, 25 penetrate the lower surface of upper vertebral endplate 43 and extensions 30, 35 penetrate the upper surface of lower vertebral endplate 45. That is, cavities are made in upper and lower endplates 43, 45 of vertebra 42 that correspond to the patterns of first extension template 27 and the second extension template. It is envisioned that instrument 40 may be inserted into cavity 50 in vertebra 42 in place of instrument 140 to manipulate punches 10, 11 such that that extensions 20, 25 penetrate the lower surface of upper vertebral endplate 43 and extensions 30, 35 penetrate the upper surface of lower vertebral endplate 45.

Figure 4:
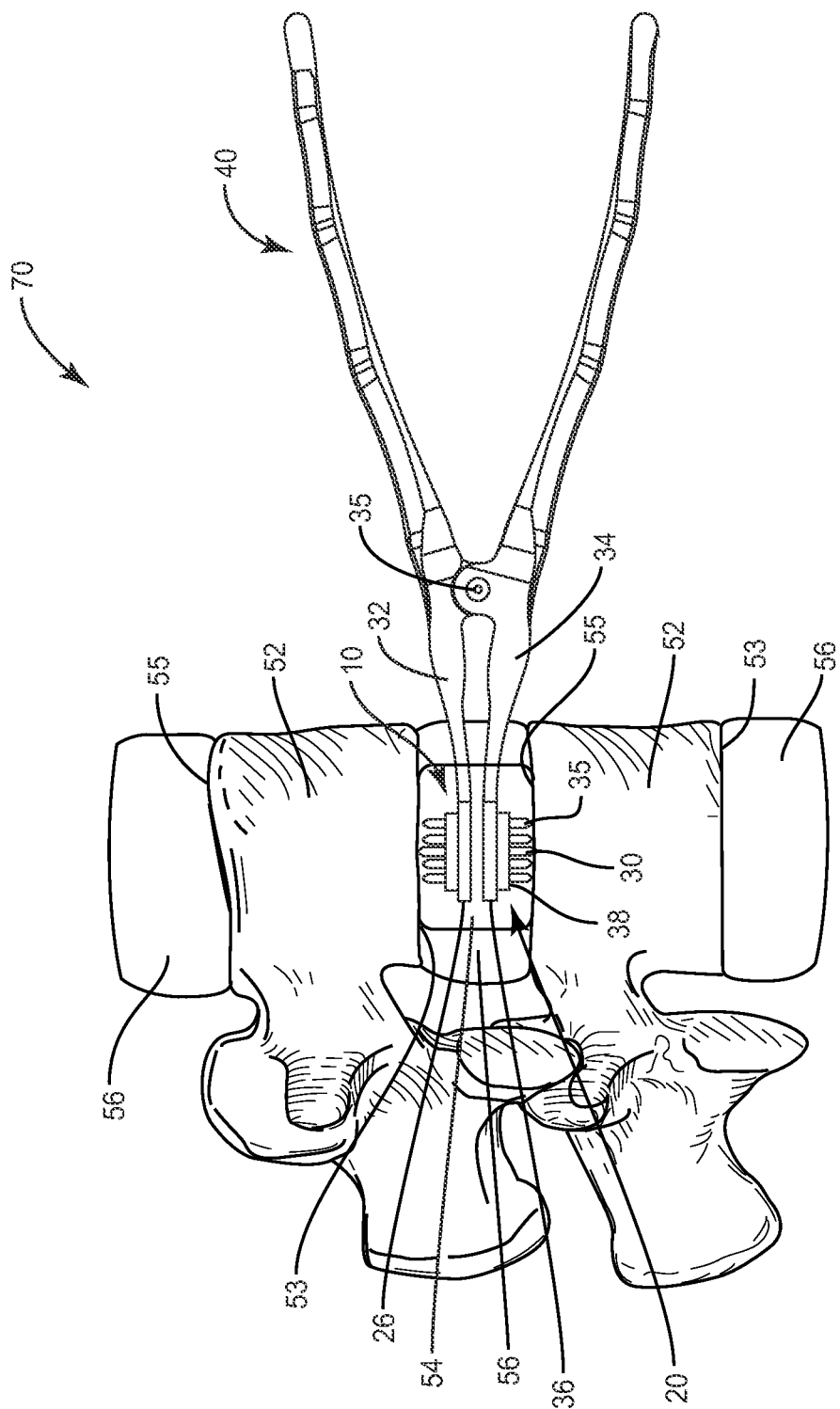
FIG. 4 is a side view of vertebrae with the instrument of FIG. 2 within the intervertebral disc.

In one embodiment, shown in FIG. 4, instrument 140 is inserted into an into an intervertebral disc 56 positioned between adjacent vertebrae 52 of a spine 70 having a plurality vertebrae 52 separated by discs 56. Each vertebra 52 extends between an upper vertebral endplate 55 and a lower vertebral endplate 53. Instrument 40 is inserted into disc 56 such that extensions 20, 25 of punch 10 are positioned adjacent a lower surface of lower vertebral endplate 53 of vertebra 52 and extensions 30, 35 are positioned adjacent an upper surface of upper vertebral endplate 55 of an adjacent vertebra 52. Proximal ends 31, 37 of instrument 40 are converged to advance punches 10, 11 away from each other such that extensions 20, 25 penetrate the lower surface of lower vertebral endplate 53 and extensions 30, 35 penetrate the upper surface of upper vertebral endplate 55 of the adjacent vertebra 52. That is, cavities are made in the lower surface of lower vertebral endplate 53 of vertebra 42 that correspond to the patterns of first extension template 27. Likewise, cavities are made in the upper surface of upper vertebral endplate 55 the adjacent vertebra 52 that correspond to the pattern of the second extension template. It is envisioned that instrument 140 may be inserted into disc 56 in place of instrument 40 to manipulate punches 10, 11 such that that extensions 20, 25 penetrate the lower surface of lower vertebral endplate 53 of vertebra 42 and extensions 30, 35 penetrate the upper surface of upper vertebral endplate 55 the adjacent vertebra 52.

Figure 5A:
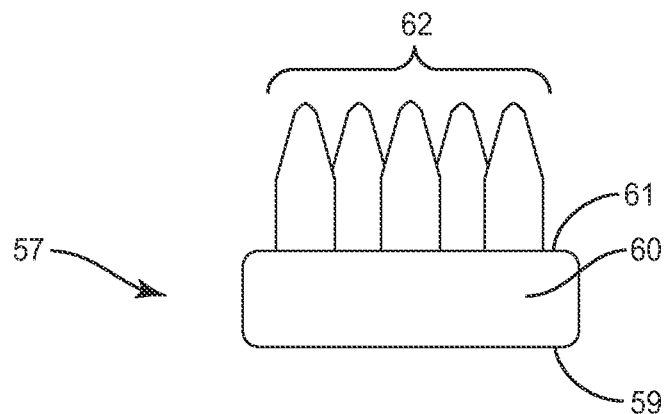
FIG. 5A is an implant having the complementary design of extensions of the endplate template on one surface.

In one embodiment, shown in FIG. 5A, the interbody implant system of the present disclosure includes an intervertebral implant 57 configured to provide height restoration between vertebral bodies, decompression and/or restoration of lordosis. Implant 57 includes a body 60 extending between a top surface 61 and a bottom surface 59. Body 61 has a plurality of extensions 62 extending from top surface 61 or bottom surface 59. As shown in FIG. 5A, extensions 62 extend from top surface 61. Extensions 62 are arranged in a pattern which is approximately the same as first template pattern 27 of punch 10 or the second template pattern of punch 20 and have a size and shape which corresponds to that of the cavities created by extensions 20, 25 or extensions 30, 35 such that extensions 62 may be received within the cavities created by extensions 20, 25 or extensions 30, 35. That is, implant 57 may be inserted into the cavities created by punch 10 or punch 11 to lock implant 57 in place and prevent slippage of implant 57 from between adjacent vertebrae.

Figure 5B:
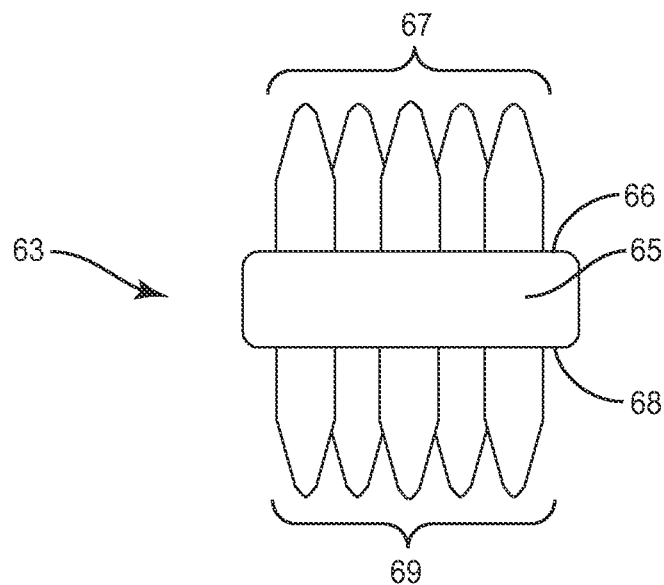
FIG. 5B is an implant having the complementary design of extensions of the endplate templates on two oppositely facing surfaces.

In one embodiment, shown in FIG. 5B, the interbody implant system of the present disclosure includes an intervertebral implant 63 configured to provide height restoration between vertebral bodies, decompression and/or restoration of lordosis. Implant 63 includes a body 65 extending between a top surface 66 and a bottom surface 68. Body 65 has a plurality of extensions 67 extending from top surface 66 and a plurality of extensions 69 extending from bottom surface 68. Extensions 67, 69 are arranged in a pattern which is approximately the same as first template pattern 27 of punch 10 or the second template pattern of punch 20 and have a size and shape which corresponds to that of the cavities created by extensions 20, 25 or extensions 30, 35, such that extensions 67, 69 may be received within the cavities created by extensions 20, 25 or extensions 30, 35. That is, extensions 67, 69 or implant 63 may be inserted into the cavities created by punch 10 and/or punch 11 to lock implant 63 in place and prevent slippage of implant 63 from between adjacent vertebrae.

Accordingly, the interbody implant system can be employed with a surgical procedure to provide height restoration between vertebral bodies for treatment of an applicable condition or injury of an affected section of a spinal column and adjacent areas within a body, such as, for example, an intervertebral disc space between the endplate of a vertebrae and the endplate of an adjacent vertebra. It is contemplated that implant 57 or implant 63 of the interbody implant system can be inserted within the intervertebral disc space to space apart articular joint surfaces, provide support and maximize stabilization of vertebrae. Implant 57 or implant 63 remains in place within the disc space and in engagement with vertebral endplates to stabilize the vertebrae in accordance with the surgical procedure. The components of implant 57 or implant 63 secure and stabilize vertebrae in connection with the surgical procedure while preventing undesired migration of implant 57 or implant 63. Implants 57, 63 can be made of radiolucent materials such as polymers. Radiomarkers may be included for identification under x-ray, fluoroscopy, CT or other imaging techniques.

In one embodiment, the components of punch 10 or punch 11, including plates 26, 36, first extension template 27 and/or the second extension template may be formed from a bioresorbable material configured to be reabsorbed over time. Accordingly, punch 10 and/or punch 11 may be positioned adjacent a vertebral endplate and advanced into the surface of the endplate to penetrate the endplate surface which creates a plurality of cavities that correspond to the pattern of first extension template 27 of punch 10 or the second extension template of punch 11. Punch 10 and/or punch 11 may then be left in situ at a location adjacent the vertebral endplate. Punch 10 and/or punch 11 will then be replaced by regenerated tissue, such as bone or cartilage tissue, for example, as punch 10 and/or punch 11 degrades. That is, the material used to form punch 10 and/or punch 11 will be degraded by cellular activity and then reabsorbed over time by tissue adjacent an intervertebral space. In one embodiment, punch 10 and/or punch 11 degrade at the rate the tissue heals.

In one embodiment, extensions 20, 25, 30, 35 are coated with at least one bone growth promoting material including, for example, bone grafts, osteoconductive materials and osteoinductive agents including morphogenic protein (BMP), cytokines, bone particles from fully mineralized bone, demineralized bone particles, autograft, allograft, xenogenic, transgenic bone particles or a combination thereof.

In one embodiment, at least one of extensions 20, 25 or extensions 30, is/are rotatable by an actuator in communication with at least one of the extensions. For example, extensions 20, 25 may extend through the surface of plate 26 opposite endplate engaging surface 15 and are able to rotate relative to plate 26. Extension 20 may have a gear including gear teeth at the end of extension 20 opposite the leading end thereof configured to rotate extension 20. At least one of extensions 25 may have a gear including gear teeth at the end of extension 25 opposite the leading end thereof configured to mate with the gear at the end of extension 20 such that the gear teeth on the gear on extension 20 engage with the gear teeth of the gear on extension 25. That is, rotating extension 20 and/or the gear at the end of extension 20 causes extension 25 to rotate as well. An actuator may be used to facilitate rotating extension 20 and/or the gear at the end of extension 20.

In assembly, operation and use, the endplate punch template and corresponding interbody implant system is employed with a surgical procedure such as a fusion treatment of a spine of a patient including vertebrae, an intervertebral disc space and body areas adjacent thereto, as discussed herein. The endplate punch template and corresponding interbody implant system may also be employed with other surgical procedures, such as, for example, discectomy, laminotomy, laminectomy, nerve root retraction, foramenotomy, facetectomy, decompression, and spinal, nucleus or disc replacement.

In one embodiment, the interbody implant system includes at least one agent, which may be disposed, packed or layered within, on or about the components and/or surfaces thereof. For example, the at least one agent is configured for disposal within extensions 20, 25, 30 or 35 or within implants 57, 63. The at least one agent can include bone growth promoting material, such as, for example, bone graft. The bone graft can be a particulate material, which may include an osteoconductive material such as hydroxyapatite and/or an osteoinductive agent such as a bone morphogenic protein (BMP) to enhance bony fixation of implants 57, 63 with adjacent vertebrae.

It is contemplated that the bone graft may include therapeutic polynucleotides or polypeptides. It is further contemplated that the bone graft may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as hydroxyapatite, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines.

It is envisioned that the agent may include one or a plurality of therapeutic agents and/or pharmacological agents for release, including sustained release, to treat, for example, pain, inflammation and degeneration. The agents may include pharmacological agents, such as, for example, antibiotics, anti-inflammatory drugs including but not limited to steroids, anti-viral and anti-retroviral compounds, therapeutic proteins or peptides, therapeutic nucleic acids (as naked plasmid or a component of an integrating or non-integrating gene therapy vector system), and combinations thereof.

The agent may also include analgesics or anesthetics such as acetic acid derivatives, COX-2 selective inhibitors, COX-2 inhibitors, enolic acid derivatives, propionic acid derivatives, salicylic acid derivatives, opioids, opioid/nonopioid combination products, adjuvant analgesics, and general and regional/local anesthetics.

The agent may also include antibiotics such as, for example, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamthoxazole, and vancomycin.

The agent may also include immunosuppressives agents, such as, for example, steroids, cyclosporine, cyclosporine analogs, cyclophosphamide, methylprednisone, prednisone, azathioprine, FK-506, 15-deoxyspergualin, prednisolone, methotrexate, thalidomide, methoxsalen, rapamycin, leflunomide, mizoribine (Bredinin™), brequinar, deoxyspergualin, and azaspirane (SKF 105685), Orthoclone OKT™ 3 (muromonab-CD3). Sandimmune™, Neoral™, Sangdya™

(cyclosporine), Prograf™ (FK506, tacrolimus), Cellcept™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrxate), Oxsoralen-Ultra™ (methoxsalen) and Rapamuen™ (sirolimus).

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An instrument for penetrating an endplate surface of a vertebra comprising:
    a first plate having an endplate engaging surface comprising a plurality of extensions projecting therefrom to form a first extension template, the first extension template including a centrally disposed extension and at least one extension radially disposed about the centrally disposed extension wherein the first extension template is configured to penetrate a first endplate surface of a vertebra when advanced into the first endplate surface of the vertebra; and
    a second plate having an endplate engaging surface comprising a plurality of extensions projecting therefrom to form a second extension template, the second extension template including a centrally disposed extension and at least one extension radially disposed about the centrally disposed extension wherein the second extension template is configured to penetrate a second endplate surface of the vertebra when advanced into the second endplate surface of the vertebra,
    wherein at least one of the plurality of extensions projecting from the first and second extension endplates is rotatable relative to the first and second plates in communication with at least one of the plurality of extensions, wherein the rotation of the at least one extension relative to the first and second plates is about a longitudinal axis of the extension which passes along a length of the extension.

2. The instrument of claim 1, wherein the first endplate surface of the vertebra is a lower vertebral endplate surface of an upper vertebral body and the second endplate surface of the vertebra is an upper vertebral endplate surface of a lower vertebral body adjacent to the upper vertebral body.

3. The instrument of claim 1, wherein the plurality of extensions projecting from the first and second extension endplates taper from a first diameter to a second diameter, wherein the first diameter is greater than the second diameter and terminate in a point configured to penetrate an endplate surface of a vertebra.

4. The instrument of claim 1, wherein the first endplate surface is a lower vertebral endplate of a vertebra and the second endplate surface is an upper vertebral endplate of the same vertebra.

5. The instrument of claim 1, wherein each of the plurality of extensions projecting from the first and second extension endplates has a cross-section selected from the group consisting of round, oval, polygonal, irregular, consistent, variable, uniform and non-uniform.

6. The instrument of claim 1, further comprising:
    a handle, a first arm, and a second arm movable towards the first arm upon actuation of the handle; and
    wherein the first plate is mounted to the first arm and the second plate is mounted to the second arm such that the plurality of extensions projecting from the first plate face away from the first arm and the plurality of extensions projecting from the second plate face away from the second arm.

7. An instrument for penetrating a vertebral endplate surface comprising:
    a first plate having a endplate engaging surface comprising a plurality of extensions projecting therefrom to form a first extension template, the first extension template including a centrally disposed extension and at least one extension radially disposed about the centrally disposed extension wherein the first extension template is configured to penetrate an endplate surface of a first vertebra when advanced into the endplate surface of the first vertebra; and a second plate having a endplate engaging surface comprising a plurality of extensions projecting therefrom to form a second extension template, the second extension template including a centrally disposed extension and at least one extension radially disposed about the centrally disposed extension wherein the second extension template is configured to penetrate an endplate surface of a second vertebra when advanced into the endplate surface of the second vertebra; wherein at least one of the plurality of extensions projecting from the first and second extension endplates is rotatable relative to the first and second plates in communication with at least one of the plurality of extensions, and wherein each of the plurality of extensions have a leading end and a trailing end separated apart from one another by a continuous wall, the leading end of each extension projecting from the first and second extension templates is configured to penetrate the endplate of the first vertebra, wherein the rotation of the at least one extension relative to the first and second plates is about a longitudinal axis of the extension which passes along a length of the extension.

8. The instrument of claim 7, wherein the first and second plates are formed from a bioreabsorbable material configured to be reabsorbed over time.

9. The instrument of claim 7, wherein the plurality of extensions projecting from the first and second extension endplates is coated with at least one bone growth promoting material selected from the group consisting of bone grafts, osteoconductive materials and osteoinductive agents including morphogenic protein (BMP), cytokines, bone particles from fully mineralized bone, demineralized bone particles, autograft, allograft, xenogenic, transgenic bone particles or a combination thereof.

10. The instrument of claim 7, further comprising:
    a handle, a first arm, and a second arm movable towards the first arm upon actuation of the handle; and
    wherein the first plate is mounted to the first arm such that the plurality of extensions projecting from the first plate face away from the first arm.

11. The instrument of claim 10, wherein the second plate is mounted to the second arm of said handle such that the plurality of extensions projecting from the second extension template face away from the second arm and when the first arm and the second arm move towards each other the first and second plates move away from each other so as to advance towards upper and lower endplates when positioned between vertebrae.

12. The instrument of claim 11, wherein the plurality of extensions projecting from the first and second extension endplates taper from a first diameter to a second diameter, wherein the first diameter is greater than the second diameter.

13. A method for penetrating a surface of a vertebral endplate comprising the steps of:
provide an instrument according to claim 11;
positioning the instrument at a location between adjacent vertebrae such that the first extension template engages a lower vertebral endplate of an upper vertebral body and the second extension template engages an upper vertebral endplate of a lower vertebral body; and
advancing the plurality of extensions projecting from the first extension template into the lower vertebral endplate and the plurality of extensions projecting from the second extension template into the upper vertebral endplate so as to penetrate the lower and upper vertebral endplates.

14. A method for penetrating a surface of a vertebral endplate comprising the steps of:
providing an instrument according to claim 8;
positioning the instrument at a location between adjacent vertebrae such that the first extension template engages a lower vertebral endplate of an upper vertebral body and the second extension template engages an upper vertebral endplate of a lower vertebral body;
advancing the plurality of extensions projecting from the first extension template into the lower vertebral endplate and the plurality of extensions projecting from the second extension template into the upper vertebral endplate so as to penetrate the lower and upper vertebral endplates; and
leaving the first plate engaged with the lower vertebral endplate and the second plate engaged with the upper vertebral endplate following the step of advancing the plurality of extensions.

15. An interbody implant system comprising:
an instrument for penetrating an endplate surface of a vertebra comprising:
a first plate having an endplate engaging surface comprising a plurality of extensions projecting therefrom, the first extension template including a centrally disposed extension and at least one extension radially disposed about the centrally disposed extension wherein the first extension template is configured to penetrate an endplate surface of a first vertebra so as to produce a complementary design to the template when advanced into the endplate surface of the first vertebra;
a second plate having a first endplate engaging surface comprising a plurality of extensions projecting from the first endplate engaging surface to form a second extension template, the second extension template including a centrally disposed extension and at least one extension radially disposed about the centrally disposed extension wherein the second extension template is configured to penetrate an endplate surface of a second vertebra so as to produce a design complementary to the template when advanced into the endplate surface of the second vertebra; and
at least one interbody implant having at least one extension on at least one surface of the interbody implant configured to mate with at least part of the complementary cavity design formed in the endplate surface of at least one of the first and second vertebrae,
wherein at least one of the plurality of extensions projecting from the first and second extension endplates is rotatable relative to the first and second plates in communication with at least one of the plurality of extensions,
wherein the rotation of the at least one extension relative to the first and second plates is about a longitudinal axis of the extension which passes along a length of the extension.

16. The interbody implant system of claim 15 wherein the first and second plates are formed from a bioreabsorbable material configured to be reabsorbed over time.

17. The interbody implant system of claim 15 wherein the second plate is mounted to the second arm of said handle such that the plurality of extensions projecting from the second extension template face away from the second arm and when the first arm and the second arm move towards each other the first and second plates move away from each other so as to advance towards upper and lower endplates when positioned between vertebrae.

* * * * *

UNITED STATES PATENT AND TRADEMARK OFFICE
CERTIFICATE OF CORRECTION

| | |
|---|---|
| PATENT NO. | : 9,301,849 B2 |
| APPLICATION NO. | : 13/829002 |
| DATED | : April 5, 2016 |
| INVENTOR(S) | : Lauryssen |

It is certified that error appears in the above-identified patent and that said Letters Patent is hereby corrected as shown below:

Specification

In Column 5, Line 45, delete "20, can" and insert -- 20, 25 can --, therefor.

In Column 8, Line 64, delete "30, such" and insert -- 30, 35 such --, therefor.

In Column 9, Line 50, delete "30, is/are" and insert -- 30, 35 is/are --, therefor.

Signed and Sealed this
Seventh Day of June, 2016

Michelle K. Lee
*Director of the United States Patent and Trademark Office*